United States Patent
Chen et al.

[11] Patent Number: 6,024,718
[45] Date of Patent: Feb. 15, 2000

[54] INTRALUMINAL DIRECTED ULTRASOUND DELIVERY DEVICE

[75] Inventors: Hank H. Chen, St. Louis, Mo.; Cheng Ji, Los Angeles, Calif.

[73] Assignee: The Regents of the University of California, Oakland, Calif.

[21] Appl. No.: 08/923,609

[22] Filed: Sep. 4, 1997

Related U.S. Application Data

[60] Provisional application No. 60/025,416, Sep. 4, 1996.

[51] Int. Cl.$^7$ .............................. A61B 17/20; A61B 17/32
[52] U.S. Cl. .............................................. 604/22; 606/169
[58] Field of Search ................................ 604/22, 49, 101, 604/128, 194; 606/169; 601/2; 600/459

[56] References Cited

U.S. PATENT DOCUMENTS

| | | |
|---|---|---|
| 4,917,097 | 4/1990 | Proudian et al. . |
| 4,936,281 | 6/1990 | Stasz . |
| 5,163,421 | 11/1992 | Berstein et al. . |
| 5,197,946 | 3/1993 | Tachibana .................................. 604/22 |
| 5,269,297 | 12/1993 | Weng et al. . |
| 5,279,546 | 1/1994 | Mische et al. . |
| 5,324,255 | 6/1994 | Passafaro et al. . |
| 5,326,342 | 7/1994 | Pflueger et al. . |
| 5,342,292 | 8/1994 | Nita et al. .................................. 604/22 |
| 5,362,309 | 11/1994 | Carter ........................................ 604/22 |
| 5,397,293 | 3/1995 | Alliger et al. . |
| 5,725,494 | 3/1998 | Brisken ...................................... 604/22 |
| 5,735,811 | 4/1998 | Brisken ...................................... 604/22 |

FOREIGN PATENT DOCUMENTS

94300846  9/1994  European Pat. Off. .

*Primary Examiner*—Corrine McDermott
*Assistant Examiner*—Michael J. Hayes
*Attorney, Agent, or Firm*—Daniel L. Dawes

[57] ABSTRACT

An ultrasound catheter comprises a coaxial cable of electrical conductors with a piezoelectric element at its distal end. The piezoelectric element is shaped and disposed according to the desired ultrasonic field. When an electrical signal from a signal generator is connected to the electrical conductors, the piezoelectric element mechanically deforms in response and generates ultrasonic energy. An alternative embodiment of the present invention is a hollow tubular catheter of flexible polymer has at its distal end a cylindrical piezoelectric element connected to electrical conductors running the length of the catheter. The piezoelectric cylinder may be tapered, segmented, shortened, etc. according to the desired focusing of the ultrasonic field, which is preferably forwardly focused. In either embodiment the catheter is threaded through a patient's vasculature and brought in close proximity to a vascular occlusion. Thrombolytic agents are released from the ultrasonic catheter or a second catheter in close proximity. These agents and ultrasonic energy from the ultrasound catheter result in breakup of the occlusion through sonophoresis.

8 Claims, 5 Drawing Sheets

INTRALUMINAL DIRECTED ULTRASOUND DELIVERY DEVICE

This application claims priority from Provisional Application No. 60/025,416, filed Sep. 4, 1996.

BACKGROUND OF THE INVENTION

1. Field of the Invention

The invention broadly relates to a device and a method for its use in assisting thrombolysis in coronary arteries, cerebral arteries, peripheral arteries, and other vascular channels. In particular, the invention relates to a piezoelectric element shaped and mounted on the tip of a wire or a catheter for the delivery of directed ultrasonic energy useful in assisting thrombolysis, endovascular sonophoresis, vascular tumor lysis, vasospasm and other medical conditions where a source of intraluminal directed ultrasound is needed.

2. Description of Related Art

Thrombolysis using pharmacologic agents and mechanical agents such as balloon angioplasty are currently the primary forms of therapy for vascular occlusions caused by thombi or thromboemboli. Their major applications are in the coronary arteries, peripheral arteries, and other vascular channels where presence of a clot (thrombus) or other occlusional deposits such as plaque result in the restriction and the blockage of blood flow. Such restriction and blockage result in oxygen deprivation of the tissue supported by the blood supply. Oxygen deprivation and its effect s are known as "ischemia". If the blood supply is completely blocked so that ischemia continues for a prolonged period of time, the affected tissue suffers permanent damage. This is what occurs in myocardial infarction and stroke. If tissue damage is extensive enough, death may ensue.

There are two general methods of administering pharmacologic agents in thrombolysis. One involves systemic infusion and the other involves local intravascular infusion. The latter requires the placement near the occlusion of a catheter through which the thrombolytic agents are delivered. Both methods are based on the principal that pharmacologic agents such as urokinase, streptokinase and recombinant tissue plasminogen activator (rt-PA) will enzymatically lyse and dissolve the occluding thrombus or thromboembolus. They can be effective, especially against newly formed thrombus. However, the administration of these drugs can cause severe bleeding complications such as cerebral hemorrhage which may result in death. Further, the effective use of these agents frequently requires prolonged treatment times (measured in hours) during which the affected tissue continues to experience ischemia.

Balloon angioplasty operates by inserting a deflated balloon through the occluded segment of a vessel. The balloon is then hydraulically inflated to stretch and compact the occlusive material and thus reopen the vessel. Balloon angioplasty can be effective but has the drawback that the thrombus is merely compacted and not actually removed. The remaining thrombus can quickly promote the reocclusion of the involved vessel. Balloon angioplasty also has the attendant risks of internal rupture or dissection of the vessel, vasospasm, and stimulation of internal hyperplasia which results in restenosis of the vessel. Furthermore, balloon angioplasty cannot be used in vessels too small for passage of the balloon catheter.

There exist other methods for reopening occluded vessels. Most of which involve mechanical devices that bore and drill through the thrombus. Because of their large caliber, inflexibility, and potential for severe damages to vessel walls, their usefulness is limited. Recently there have been a number devices have been developed that utilize ultrasonic energy to break up thrombus and other occluding materials. The general design involves an extracorporeal transducer coupled to a solid metal wire which is threaded through the vessel and placed in contact with the occlusion. Ultrasonic energy generated by the transducer is conducted along the solid metal wire to its up. The tip, vibrating at around 20–30 kHz, strikes the occlusive material and causes it to break up largely through mechanical interaction. Because ultrasonic energy must be efficiently transmit along considerable distances, the wires (usually of titanium or aluminum alloy) are relatively stiff and have relatively large diameters. Therefore, these ultrasonic devices cannot be effectively steered into tortuous or small vessels. The stiffness of the solid transmission wires also increases the potential for vessel wall injuries such as dissection and rupture. The other problem facing this type of design is that the tip of the wire vibrates mostly in a longitudinal fashion so that the ultrasonic energy cannot be effectively focused or directed. Examples of this type of design can be found in U.S. Pat. No. 5,269,297 to Weng, U.S. Pat. No. 5,326,342 to Pflueger, and U.S. Pat. No. 5,397,293 to Alliger.

In other attempts to utilize ultrasonic energy to reopen occluded vessels, a number of in vitro experiments have examined the effect of external ultrasonic irradiation on thrombolysis by pharmacologic agents. Such study is described in Lauer, CG et al:, Effect of ultrasound on tissue-type plasminogen activator-induced thrombolysis. Circulation. 86(4): 1257–1264, 1992. The results of these studies indicate that the combination of ultrasound and pharmacologic agents greatly accelerates the process of thrombolysis. Unlike the ultrasonic transmission wire described above, there is no direct mechanical disruption of thrombus in this method because there is no physical contact between the ultrasound delivery device and the thrombus. Ultrasonic energy impinging on the thrombus is transmitted through a liquid medium from a transducer. The exact mechanism of thrombolysis enhancement by ultrasonic irradiation is still under investigation, but it is thought that ultrasound facilitates the penetration of pharmacologic agents into the thrombus. Because the lytic action of these agents is surface area dependent, greater permeation means faster thrombolysis.

There are catheters with ultrasonic transducer at their tip such as the catheter disclosed in U.S. Pat. No. 4,917,097 to Proudian. These catheters are used for ultrasonic imaging of vessels, and because these catheters are designed for imaging purposes, ultrasonic generating piezoelectric elements are disposed to direct most of the generated high frequency ultrasonic energy toward the vessel walls. Further, because the piezoelectric elements of these catheters must also function as receivers of ultrasonic signals bounced back from the vessel walls, the devices are unable to deliver relatively high intensity ultrasonic energy. The amplitude of the ultrasound is reduced because the piezoelectric elements must stop emitting ultrasonic energy during the time they act as signal receivers.

Experimental research has shown that significant enhancement of thrombolysis occurs using ultrasonic intensity well above that used for imaging purposes (Olsson SB et al., Enhancement of thrombolysis by ultrasound, Ultrasound in Medicine and Biology, 20(4):375–382, 1994). Therefore, the low amplitude ultrasonic transducers of these imaging catheters cannot, nor are they intended to, enhance thrombolysis. The energy conversion efficiencies of ultrasound imaging transducers are generally not high enough to be used at the levels needed for thrombolysis, and such imaging transducers could be destroyed by the generated heat at the energy levels needed for thrombolysis.

Furthermore, many of these catheters have integrated circuitry in their tips and contain transmission cables comprising a large number conductors, all of which result in inflexible catheters with relatively large diameter. In fact, to obtain adequate imaging resolution as many as 32–64 sensors and their corresponding sensing wires must be included in the catheter. Even when the signal is multiplexed by tip circuitry, the minimum number of catheter wires still remains at eight, which together with the bulk of the electronic circuitry virtually excludes the use of such catheters in small or tortuous vessels.

While it has been demonstrated that ultrasonic irradiation enhances pharmacologic thrombolysis, and while ultrasound energy can be transmitted from the tip of a catheter for imaging purposes, no effective means of delivering ultrasound energy to a thrombotic vessel for pharmacologic thrombolysis is presently available. For this purpose one needs a flexible, minimal profile ultrasound delivery device that is capable of navigating small, tortuous channels in order reach the thrombotic site. Further, this device must be capable of delivering ultrasonic energy in a directed fashion at a relatively high amplitude while, at the same time, delivering thrombolytic agents. Such a device would enhance the procedure of pharmacologic thrombolysis by reducing the treatment time and/or the amount of pharmacologic agents administered. These reductions would minimize the potential for severe complications.

OBJECTS AND SUMMARY OF THE INVENTION

It is the object of the present invention to provide a flexible, minimal profile wire or catheter for ultrasound delivery capable of navigating small and tortuous vessels;

It is also the object of the present invention to provide an ultrasonic generating element placed on the distal tip of a wire or catheter capable of delivering high amplitude ultrasonic energy in broadband frequency for enhancing pharmacologic thrombolysis;

It is a further object of the present invention to provide an ultrasonic generating element shaped and placed on the distal tip of the wire in such a fashion to allow directional emission of ultrasonic energy; and A more particular object of the present invention is to provide such a catheter with a tapered distal end useful for both infusion of fluid and aspiration of small particles.

These and additional objects are met by an ultrasound catheter comprising a coaxial cable of electrical conductors with a piezoelectric element at its distal end. The piezoelectric element is shaped and disposed according to the desired ultrasonic field. When an electrical signal from a signal generator is connected to the electrical conductors, the piezoelectric element mechanically deforms in response and generates ultrasonic energy. An alternative embodiment of the present invention is a hollow tubular catheter of flexible polymer has at its distal end a cylindrical piezoelectric element connected to electrical conductors running the length of the catheter. The piezoelectric cylinder may be tapered, segmented, shortened, etc. according to the desired focusing of the ultrasonic field, which is preferably forwardly focused. In either embodiment the catheter is threaded through a patient's vasculature and brought in close proximity to a vascular occlusion. Thrombolytic agents are released from the ultrasonic catheter or a second catheter in close proximity. These agents and ultrasonic energy from the ultrasound catheter result in breakup of the occlusion through sonophoresis.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings where like elements are referenced by like numerals.

The invention and its various embodiments can now be understood by considering the following detailed description.

DETAILED DESCRIPTION OF THE PREFERRED EMBODIMENTS

The following description is provided to enable any person skilled in the art to make and use the invention and sets forth the best modes contemplated by the inventors of carrying out their invention. Various modifications, however, will remain readily apparent to those skilled in the art, since the general principles of the present invention have been defined herein specifically to provide a catheter that provides delivery of both ultrasonic energy and thrombolytic agents for ultrasonically enhanced thrombolysis.

In general terms, the invention is a catheter with a focused, high intensity ultrasound producing element positioned on its tip and forwardly focused into the thrombic mass. More particularly, the invention comprises a forwardly focused ultrasound producing element capable of outputting 0.5 to 2 watts of ultrasound energy with an overall diameter of the order of one millimeter or less and preferably 0.5 mm for use in the coronary and cerebral arteries. As a result of this small diameter, the catheter is flexible enough to permit insertion into the tortuous paths of small vessels with minimal vasospastic reaction.

The invention is used for the direct fracture and removal of brittle thrombi by high intensity forwardly focused or concentrated ultrasound, and additionally contemplates the combined use of medicines for sonophoresis or deep infusion and delivery of fibrinolytic agents and thrombolysis of soft, adherent thrombi.

In its preferred implementation the device of the present invention comprises of a coaxial cable that has electrical conductors. At the distal end of the coaxial wire is a piezoelectric element which is shaped and placed according to the desired ultrasonic field. When an electrical signal from a signal generator connected to the proximal end of the device, is sent along the two conductors, a signal potential is generated across the piezoelectric element which will mechanically deform in response to the changing potential and generate ultrasonic energy.

In an alternative embodiment of the present invention, a catheter of flexible polymer has at its distal end a cylindrical piezoelectric element. The piezoelectric cylinder may be tapered, segmented, shortened, etc. according to the desired focusing of the ultrasonic field, which is preferably forwardly focused. This piezoelectric material is sandwiched between two layers of conductive material. Two wires, running along the length of the catheter, are each connected to one of two layers of the conductive material. When a signal generator at the proximal end of the catheter sends electrical energy along the two wires, a signal potential will exists across the piezoelectric material which then generates ultrasonic energy.

Figure 1:
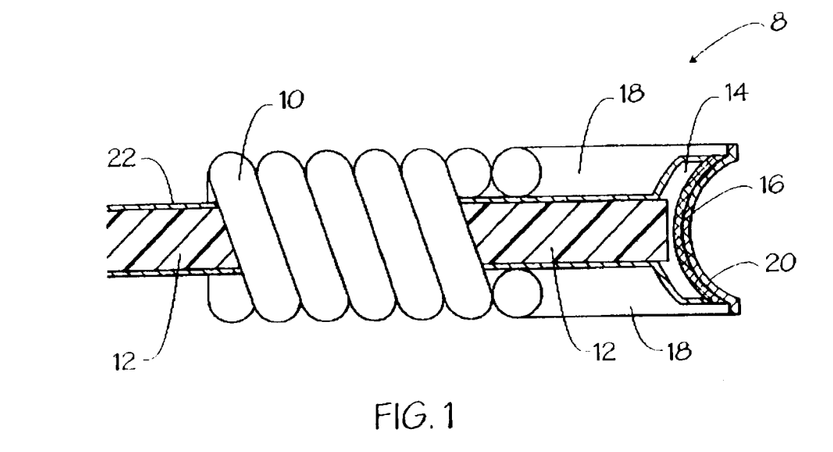
FIG. 1 is a partially cutaway side view of the catheter tip in enlarged scale showing a coaxial conductor connected to a transducer with a concave-shaped surface.
Figure 2:
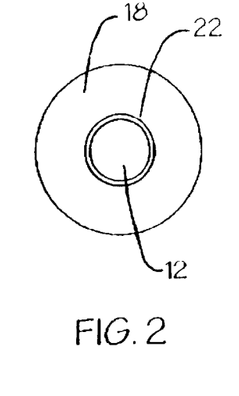
FIG. 2 is a perpendicular cross-sectional view of FIG. 1 taken through lines 2—2.

Turning to FIG. 1, which is a partially cutaway side view in enlarged scale of a tip of an ultrasound catheter 8, the device according to the present invention has two conductors 10 and 12 that are electrically isolated from each other by an insulating coating 22 such as TEFLON brand perfluorocarbon coating as best illustrated in the cross-sectional view of FIG. 2 taken through lines 2—2 of FIG. 1. The conductors 10 and 12 are made of metal such as stainless steel or any other suitable material. The first conductor 10 is coiled around the second conductor 12 to minimize the device's diameter while providing appropriate stiffness and flexibility. This device is preferably used by being inserted through a guide catheter 13. Such an arrangement is well known in the art of guidewire construction.

Figure 3:
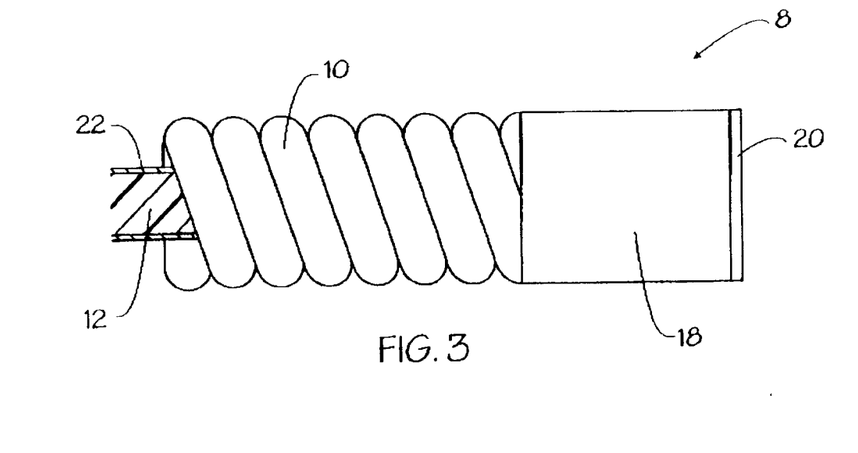
FIG. 3 is a side elevational view of the catheter tip of FIG. 1.
Figure 4:
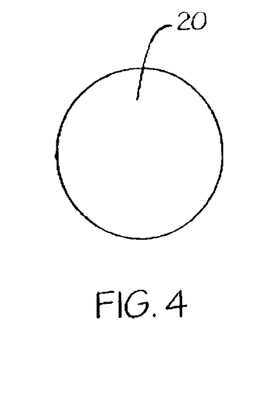
FIG. 4 is an end elevational view of the catheter tip of FIG. 1 as seen through section lines 4—4 of FIG. 3.

At the very tip of the device 8 is an ultrasonic transducer 16. The transducer 16 should be ruggedized, better heat protected, thicker, or more robustly made or supported as compared to ultrasonic imaging transducers of the prior art, since energy outputs of the transducer 16 in the present application will be substantially greater than experienced in the ultrasound imaging art. The transducer 16 is covered on its outer surface by a layer of conductive material 20 such as conductive epoxy or metallic coating. The conductive layer 20 is electrically connected to the first conductor 10 by a conductive cylinder 18 preferably made from platinum because platinum is very radio-opaque. Strong radio-opacity makes the tip of the device 8, as shown in side elevational view in FIG. 3 and end elevational view in FIG. 4, easy to identify fluoroscopically from all directions.

On the inner surface of the piezoelectric element 16 is a backing layer of a conductive material 14 such as conductive epoxy. The conductive backing layer 14 in turn is connected to the second conductor 12. Thus, the ultrasonic transducer 16 is the only electrical connection or path between the conductors 10 and 12. The proximate ends of the conductors 10 and 12 are connected to an appropriate signal generator and amplifier, preferably external to the patient.

The ultrasonic transducer 16 may be made of any material possessing piezoelectric properties. Many materials are suitable such as piezoelectric zirconium titanate (PZT) and polyvinylidene difluoride (PVDF). Appropriate thickness of the transducer 16 can be manufactured by processes well known in the art so that the thickness corresponds to the desired resonant frequency.

Figures 7, 8:
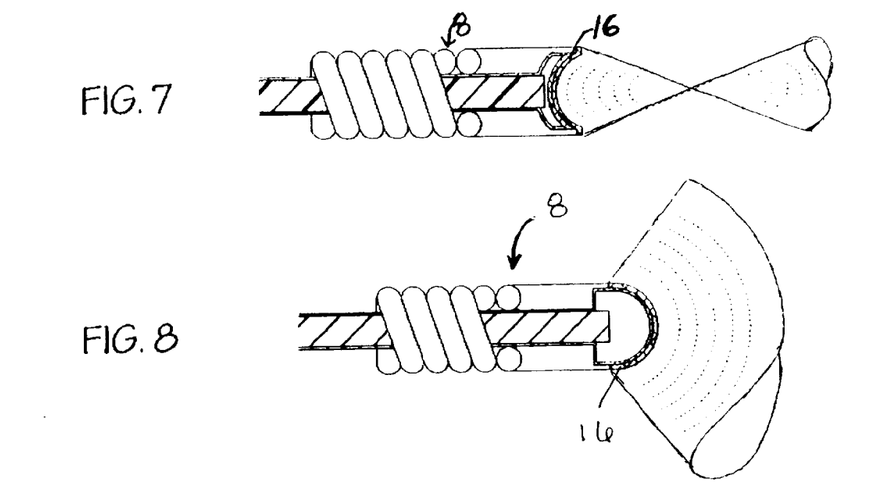
FIG. 7 is a diagram illustrating the focused ultrasound field of the concave tip of FIGS. 1–4.
FIG. 8 is a diagram illustrating the focused ultrasound field of the convex tip of FIG. 5.

The transducer 16 can be shaped and positioned in a manner that gives the emitted ultrasound directionality. For example, in FIGS. 1–4 the ultrasonic transducer 16 has a concave shape and therefore is able to focus the ultrasonic waves or energy in a forward direction as illustrated in FIG. 7. Field power intensities in excess of what are attainable at the surface of the transducer 16 can, therefore, be achieved.

Figure 5:
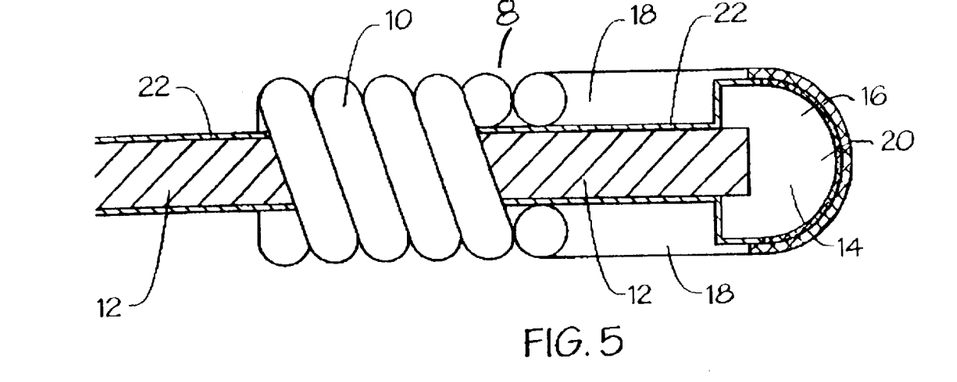
FIG. 5 is a partially cutaway side view of another embodiment of the catheter tip in enlarged scale showing a coaxial conductor connected to a transducer with a convex-shaped surface.
Figure 9:
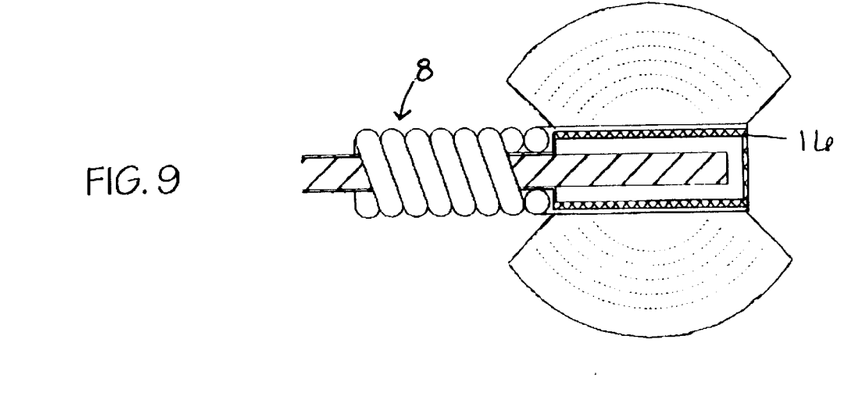
FIG. 9 is a diagram illustrating the focused ultrasound field of the cylindrical tip of FIG. 6.

FIG. 5 shows another embodiment of the distal end of the present invention where the ultrasonic transducer 16 has a convex shape and, therefore, is able to emit ultrasound waves or energy in a wide diverging forwardly focused conical field as diagrammatically seen in FIG. 8. In still another embodiment, shown in FIG. 6, the ultrasonic transducer 16 is tube-shaped and, therefore, has a cylindrical field of energy as diagrammatically shown in FIG. 9.

Figure 6:
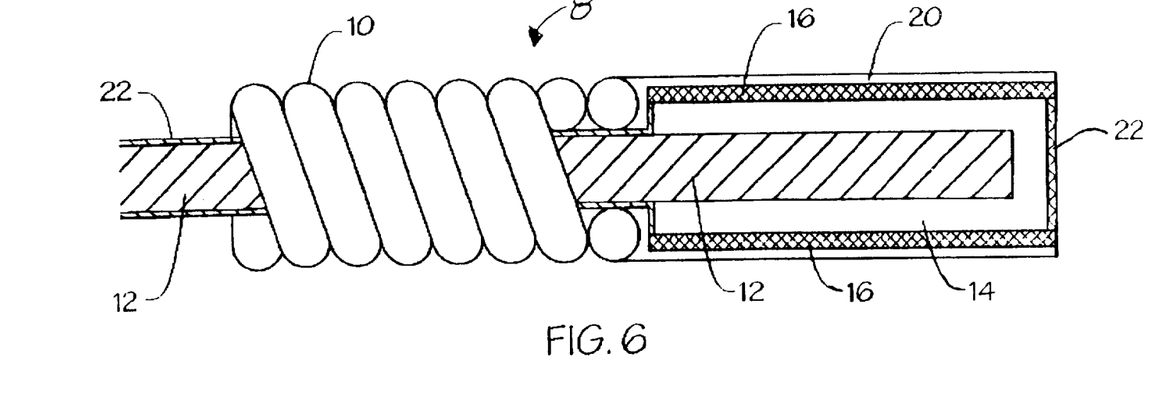
FIG. 6 is a partially cutaway side view of yet another embodiment of the catheter tip in enlarged scale showing a coaxial conductor connected to a transducer with a cylindrically-shaped surface.

Whereas FIG. 6 shows the tip having a solid fill of conductive epoxy material 14 between the conductor 12 and the transducer 16, it is also possible that all or a portion of the space filled by the conductive material 14 may be empty or filled with a compressible material or gas, which allows even greater energy outputs to be realized from the transducer 16. In such a case, electrical connection between the conductors 12 and the transducer 16 is either provided by a partial radially extending bridge of conductive material 14 disposed between conductor 12 and the transducer 16 or the conductor 16 may be indirectly connected such as through a wire bond to transducer 16, or directly connected such as by being bent and soldered or conductively epoxied thereto.

Figure 12:
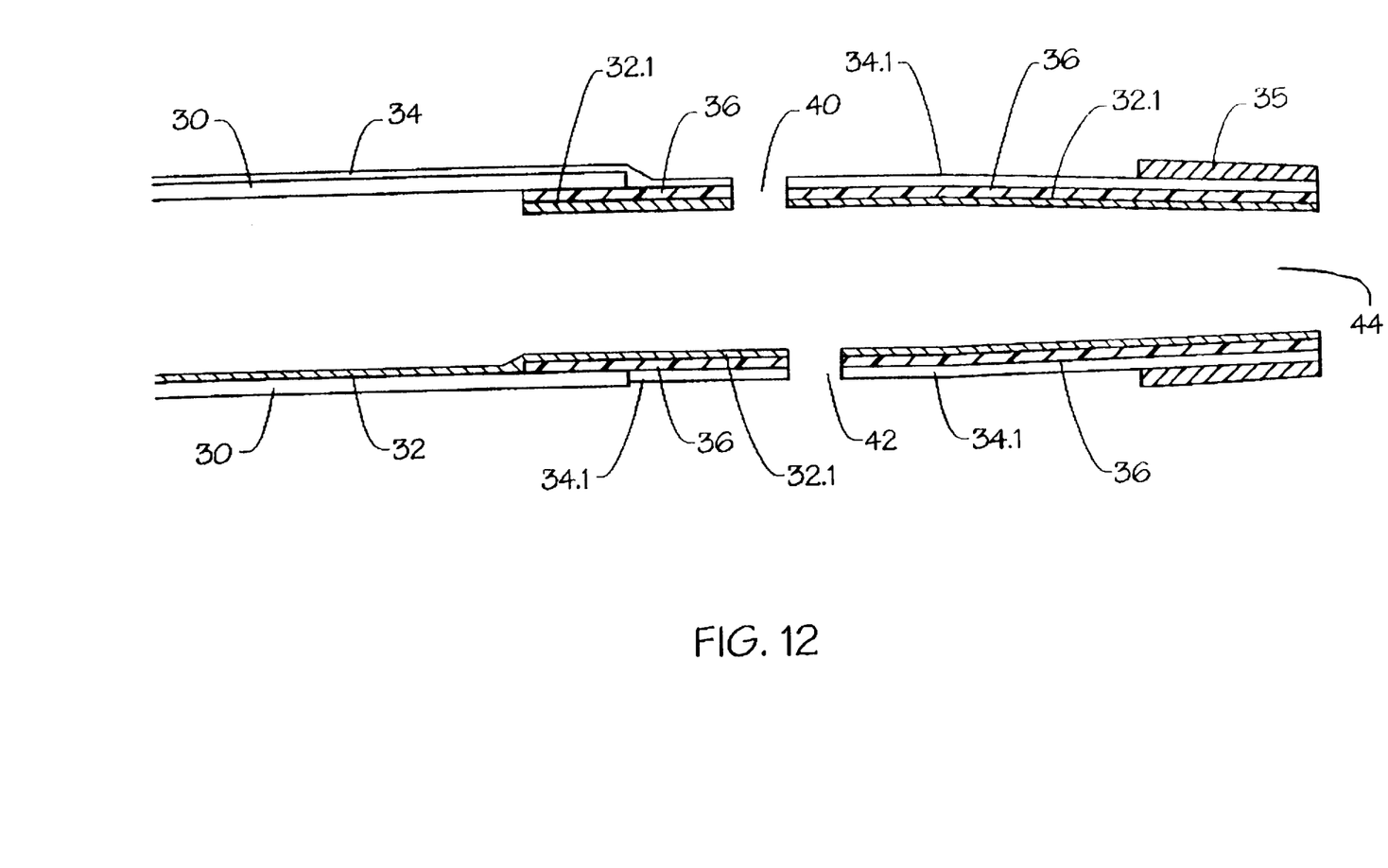
FIG. 12 is a cutaway side view of still another embodiment of the catheter tip in enlarged scale showing a coaxial conductor connected to a hollow and tapered cylindrically shaped transducer surface.

FIG. 12 is a cross-sectional side view in enlarged scale of an alternative embodiment of the invention, which has a piezoelectric element 36 on the distal end of a catheter 30 made of a polymer commonly used in the art of catheter manufacturing. The shape of the piezoelectric element 36 may be cylindrical, fabricated from an array of strips or multi-ringed segments, and generally made from any number of components and shapes according to the desired ultrasound field to be generated thereby. In FIG. 12, the piezoelectric transducer 36 takes the shape of a cone tapering toward the distal end of the catheter 30. The transducer 36 is inserted into the distal end of the catheter 30 and secured with a thin layer of epoxy glue. The transducer 36 is sandwiched between two thin layers of conductive material, an inner conductor 32.1 and an outer conductor 34.1. One of these two conductive layers is preferentially composed of a radio-opaque material such as platinum. It is also possible to put a radio-opaque sheath 35 covering the all or part of the transducer 36. The two layers 32.1, 34.1 are connected to the conductor wires 32 and 34 which run longitudinally along the length of the catheter 30. In the illustrated embodiment the first wire 32 is disposed inside the catheter 30 and the second wire 34 is disposed outside the catheter 30. At the proximal end of the catheter 30 exterior to the patient, the conductor wires 32 and 34 are connected to a signal generator. A lumen 44 of the catheter 30 allows insertion of a guidewire, and fluid infusion as well as fluid aspiration. The side holes 40 and 42 allows fluid infusion in the event that the distal opening of the catheter 30 is occluded.

Figure 10:
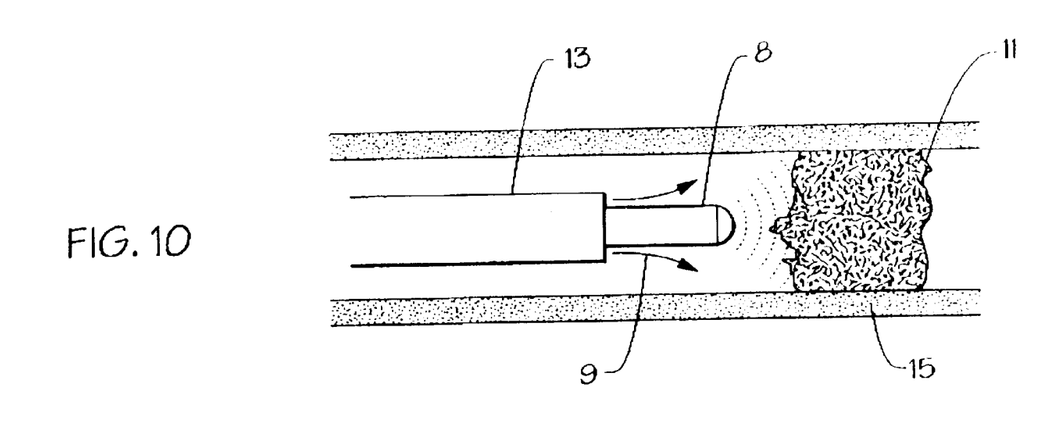
FIG. 10 is a diagram illustrating the use of the catheter tip of FIG. 8 for ultrasonically fracturing and/or sonophoretically infusing a hard occluding thrombus.

According to the method of use as shown in FIG. 10, the ultrasound catheter 8 is positioned next to a thrombus 11 in a vessel 15 by means of a conventional guiding catheter 13 which has previously been placed in the vessel 15 by a percutaneous transluminal method well known in the art. The procedure visualized by fluoroscope or other imaging method. Ultrasound energy is emitted from the tip of the device while a pharmacologic thrombolytic agent such as urokinase or rt-PA is infused through the guiding catheter 13 as diagrammatically indicated by the arrows 9 in FIGS. 10 and 11. By facilitating the permeation of thrombolytic agents into the thrombus 11, ultrasonic energy accelerates the process of thrombolysis and achieves vessel reopening in a shorter time and/or with smaller amounts of thrombolytic agent by a process known as sonophoresis, which heretofore was generally only practiced using an exterior ultrasound source.

Figure 11:
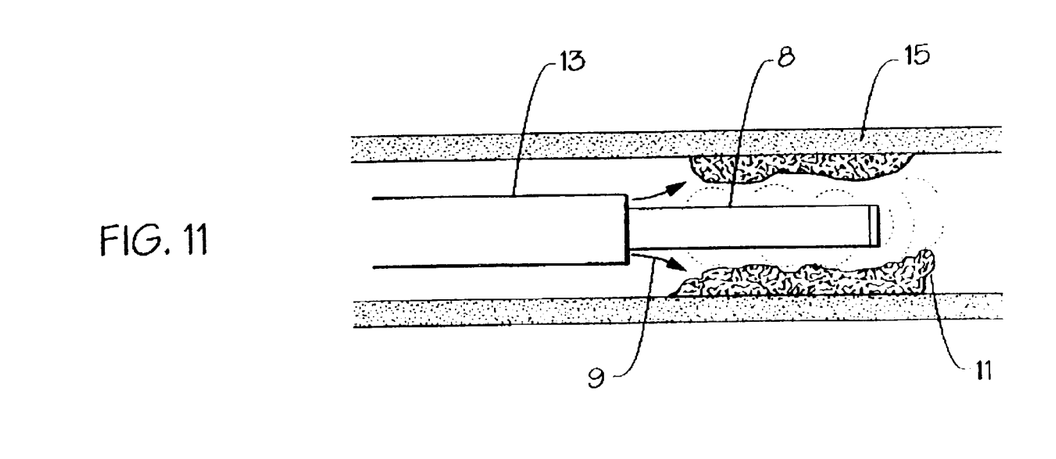
FIG. 11 is a diagram illustrating the use of the catheter tip of FIG. 6 for ultrasonically fracturing and/or sonophoretically infusing a hard occluding thrombus into which an initial penetration by the tip is made.

The ultrasound catheter 8 as shown in FIGS. 10 and 11 is advanced to the site of thrombotic occlusion 11 via the guiding catheter 13. The ultrasound catheter 8 is then inserted into the thrombus 11 through a channel previously created by pushing a guidewire (not shown) against the thrombus 11 as shown in FIG. 11. If the guidewire is not able to traverse the thrombus 11, an attempt will be made to traverse the thrombus 11 using ultrasound or sonophoresis. Through exposure to thrombolytic agents and high intensity ultrasonic energy emitted from the catheter, the thrombus 11 can be made more passable. In any case, the sonophoresis effect quickly dissolves fragments of the thrombus 11 that are mechanically released, thereby preventing their accidental release into the circulatory system. In addition, released fragments of the thrombus 11 can be aspirated through the guide catheter 13.

It is within the scope of the invention that the embodiments of FIGS. 1, 5, 6 and 12 may be combined and activated separately or in conjunction with each other. For example, a forwardly focusing transducer on the tip may be first used for thrombus penetration as shown in FIG. 10. Then the ultrasound catheter 8 can be withdrawn and replaced with the catheter 8 a cylindrical transducer like that shown in detail in FIG. 6 which is used to sonophoretically remove the thrombus 11 as shown in FIG. 11.

Once the catheter 8 is inside the thrombus 11, thrombolytic agents can be infused through the guide catheter 13. An even more preferable arrangement is to insert an ultrasound catheter 30 or the type shown in FIG. 12 so that thrombolytic agents can be infused through the distal opening 44 and the side holes 40, 42 while emitted ultrasonic energy from the transducer 36 facilitates the permeation of the thrombolytic agents. Depending on the composition of thrombus, ultrasound energy may also be able to break up thrombus into smaller pieces. Aspiration through the catheter lumen is applied in such instances to remove small particles and thus prevent their movement downstream in the circulatory system. While the particles are being aspirated through the tip of the catheter 30, they are further exposed to ultrasonic energy. This causes them to break up into even smaller particles which prevents the occlusion of the catheter. A tapered distal end of the catheter 30 helps in preventing occlusion by large particles by permitting the fragments, if any, which are aspirated to move into an expanding space in the lumen rather than jamming or being compress by a fluid aspiration into a constricting space.

Ultrasound at high intensity can have an adverse biological effect. Much of the ultrasound energy is converted to heat which has adverse thermal effects on tissue and biological materials. Second, cavitation can be created by high intensity ultrasound which causes the implosive contraction of bubbles in the blood or bodily fluids with locally destructive effects. Third, ultrasound energy fields can cause micros/reaming, which is a phenomena whereby strong local sheer pressure waves can be created with physically destructive effect. The ultrasound catheters 8, 30 of the disclosed embodiments avoids unnecessary exposure of healthy tissues to high intensity ultrasound energy and its adverse biological effects described above, and uses these effects to only obtain the desired thrombolysis instead.

Many alterations and modifications may be made by those having ordinary skill in the art without departing from the spirit and scope of the present invention. The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself. The definitions of the words or elements of the following claims are, therefore, defined in this specification to include not only the combination of elements which are literally set forth, but all equivalent structure, material or acts for performing substantially the same function in substantially the same way to obtain substantially the same result.

In addition to the equivalents of the claimed elements, obvious substitutions now or later known to one with ordinary skill in the art are defamed to be within the scope of the defined elements. The claims are thus to be understood to include what is specifically illustrated and described above, what is conceptually equivalent, what can be obviously substituted and also what essentially incorporates the essential idea of the invention. Those skilled in the art will appreciate that various adaptations and modifications of the just-described preferred embodiment can be configured without departing from the scope and spirit of the invention. The illustrated embodiment has been set forth only for the purposes of example and that should not be taken as limiting the invention. Therefore, it is to be understood that, within the scope of the appended claims, the invention may be practiced other than as specifically described herein.

We claim:

1. An improved method for opening occluded vascular elements of the type wherein ultrasound and thrombolytic agents are used to dissolve an occlusion, the improvement comprising the steps of:

inserting an ultrasound catheter having a longitudinal axis including a shaped, distally disposed and forwardly oriented piezoelectric ultrasound generating tip into a patient's vascular system so that the tip of said catheter is in proximity to a vascular occlusion;

energizing the shaped piezoelectric ultrasound generating tip to radiate concentrated wavefronts of a forwardly focussed beam of ultrasound energy from said transducer toward said occlusion in the direction of said longitudinal axis; and releasing thrombolytic agents in proximity of said occlusion so that sonophoresis of said occlusion occurs.

2. A method for removing an occlusion from a patient's vascular system comprising the steps of:

inserting an ultrasound catheter into a patient's vascular system, the catheter comprising:
an elongate body containing two electrical conductors connected to a signal generator;
a shaped piezoelectric transducer disposed at a distal end of the elongate body in electrical communication with the conductors, said shaped piezoelectric transducer having a shape and orientation on said distal end which longitudinally and forwardly directs a focussed ultrasound beam in concentrated wavefronts toward said occlusion to concentrate ultrasound power of said transducer to increase energy intensity in a defined forward direction; and
radio-opaque material covering at least a portion of the transducer;
monitoring the position of the transducer fluoroscopically and bringing it into the proximity with a vascular occlusion;
infusing thrombolytic agents into contact with the vascular occlusion; and
energizing the piezoelectric transducer to forwardly radiate said focussed ultrasonic beam generated by the transducer into said vascular occlusion in combination with the thrombolytic agents to disperse the occlusion through sonophoresis.

3. An ultrasound catheter for removing vascular occlusions through sonophoresis for use with a signal generator comprising:

an elongate catheter body comprised of two conductors separated by an electrically insulating material and connected to said signal generator;
a shaped piezoelectric ultrasound transducer at a distal end of the catheter body in which a shape is defined for said shaped piezoelectric ultrasound transducer to radiate a a focussed beam of ultrasound energy from said piezoelectric ultrasound transducer in a forwardly concentrated beam in which concentrated wavefronts are directed toward said occlusion to concentrate ultrasound power of said transducer to increase energy intensity in a defined forward direction, a first surface of the shaped piezoelectric ultrasound transducer in electrical contact with a first of the conductors and a second surface in electrical contact with a second of the conductor; and
a radio-opaque material surrounding the shaped piezoelectric ultrasound transducer.

4. An ultrasound catheter for removing a vascular occlusion through sonophoresis used in combination with a signal generator comprising:

an elongate tubular catheter body having a central lumen;
two electrical conductors running the length of the catheter body and connected to said signal generator;
a hollow cylindrical ultrasound transducer having two open ends and an inner and outer surface, said hollow cylindrical ultrasound transducer disposed at a distal end of the catheter body with the central lumen of the catheter body in fluidic communication with one of the open ends of the hollow cylindrical transducer, said inner surface of the transducer in electrical communication with a first of the two electrical conductors and said outer surface of the transducer in electrical communication with a second of the two electrical conductors, wherein the ultrasound transducer is a hollow truncated cone so that a terminal opening of the transducer has a smaller inner diameter than an inner diameter of the catheter body such said hollow truncated cone directs an increased portion of ultrasound energy output by said ultrasound transducer forwardly in the direction of said occlusion as compared to a cylindrical transducer, while still maintaining a high degree of fluidic communication through said hollow cylindrical ultrasound transducer in the direction of said occlusion; and
a radio-opaque material surrounding at least part of the transducer.

5. An ultrasound catheter for removing vascular occlusions through sonophoresis comprising:

an elongate catheter body comprised of two conductors separated by an electrically insulating material;
a piezoelectric ultrasound transducer having a forwardly disposed primary radiating surface at a distal end of the catheter body, positioned on said distal end to radiate a focussed beam of ultrasound energy in concentrated wavefronts toward said occlusion to concentrate ultrasound power of said transducer to increase energy intensity in a defined forward direction, a first surface of the transducer in electrical contact with a first of the conductors and a second surface in electrical contact with a second of the conductor; and
a radio-opaque material surrounding the transducer.

6. The ultrasound catheter of claim 5, wherein the distal end of the catheter is concave in cross-section.

7. The ultrasound catheter of claim 5, wherein the distal end of the catheter is convex in cross-section.

8. An ultrasound catheter for removing vascular occlusions through sonophoresis comprising:

an elongate tubular catheter body having a central lumen;
two electrical conductors running the length of the catheter body;
a hollow cylindrical ultrasound transducer disposed at a distal end of the catheter body with the lumen of the catheter body in fluidic communication with one of the open ends of the cylindrical transducer, one surface of the transducer in electrical communication with a first of the conductors and a second surface of the transducer in electrical communication with a second of the conductors, wherein the ultrasound transducer is a hollow truncated cone so that a terminal opening of the transducer has a smaller inner diameter than an inner diameter of the catheter body; and
a radio-opaque material surrounding at least part of the transducer.

* * * * *